US008173576B2

(12) United States Patent
Maekawa et al.

(10) Patent No.: US 8,173,576 B2
(45) Date of Patent: May 8, 2012

(54) METHOD OF PRODUCING SUSPENDED AGRICULTURAL CHEMICAL COMPOSITION

(75) Inventors: Yuichi Maekawa, Fujieda (JP); Seizo Hashimoto, Odawara (JP); Roy C. Y. Chen, Raleigh, NC (US)

(73) Assignee: Nippon Soda Co., Ltd., Tokyo (JP)

( * ) Notice: Subject to any disclaimer, the term of this patent is extended or adjusted under 35 U.S.C. 154(b) by 1113 days.

(21) Appl. No.: 11/915,430

(22) PCT Filed: May 11, 2006

(86) PCT No.: PCT/US2006/018364

§ 371 (c)(1),
(2), (4) Date: Feb. 21, 2008

(87) PCT Pub. No.: WO2006/127298

PCT Pub. Date: Nov. 30, 2006

(65) Prior Publication Data

US 2008/0274890 A1 Nov. 6, 2008

Related U.S. Application Data

(63) Continuation of application No. 11/139,264, filed on May 26, 2005, now abandoned.

(51) Int. Cl.
*A01N 25/00* (2006.01)
*A01N 43/40* (2006.01)

(52) U.S. Cl. .................... 504/116.1; 504/130; 504/244; 504/249

(58) Field of Classification Search .................. 504/116, 504/130, 244, 249, 358, 362; 424/173, 200, 424/220, 249, 274, 286, 300, 326
See application file for complete search history.

(56) References Cited

U.S. PATENT DOCUMENTS

| | | | | |
|---|---|---|---|---|
| 4,348,385 | A | 9/1982 | Synek | |
| 5,547,918 | A * | 8/1996 | Newton et al. | 504/361 |
| 5,869,427 | A | 2/1999 | Yoshikawa et al. | |
| 5,906,962 | A | 5/1999 | Pallas et al. | |
| 6,187,944 | B1 | 2/2001 | Koyanagi et al. | |
| 6,767,865 | B2 * | 7/2004 | Den Tandt et al. | 504/362 |

FOREIGN PATENT DOCUMENTS

| | | |
|---|---|---|
| JP | S57-109701 | 7/1982 |
| JP | 5-25011 A | 2/1993 |
| JP | 2001-342102 A | 12/2001 |

OTHER PUBLICATIONS

Pesticide Formulation Processing Technology 2$^{nd}$ Edition, Chemical Industry Press, LIU Bulin, 2002, p. 324, with English translation.

* cited by examiner

*Primary Examiner* — Johann Richter
*Assistant Examiner* — Jane C Oswecki
(74) *Attorney, Agent, or Firm* — Foley & Lardner LLP

(57) ABSTRACT

A method of producing a suspended agricultural chemical composition, includes the steps of: grinding an agricultural chemical active ingredient; mixing at least water, a polyalcohol, a mineral salt, and a surfactant to produce a solution; adding to the solution the ground agricultural chemical active ingredient and a suspension stabilizer, to produce a mixture; heating the mixture to 40 to 70° C. while stirring; cooling the heated mixture to 10 to 25° C.; and wet-milling the cooled mixture at 30° C. or below. Alternatively the method includes the steps of: grinding an agricultural chemical active ingredient; mixing at least water, a polyalcohol, a mineral salt, and a surfactant to produce a solution; adding to the solution the ground agricultural chemical active ingredient and a suspension stabilizer to produce a mixture; wet-milling the mixture; heating the wet-milled mixture to 40 to 70° C. while stirring; and cooling the heated mixture.

20 Claims, No Drawings

METHOD OF PRODUCING SUSPENDED AGRICULTURAL CHEMICAL COMPOSITION

CROSS-REFERENCE TO PRIOR APPLICATION

This is a U.S. National Phase Application under 35 U.S.C. §371 of International Patent Application No. PCT/US2006/018364 filed May 11, 2006, which claims priority to U.S. patent application Ser. No. 11/139,264, filed May 26, 2005. Both of these applications are incorporated by reference herein. The International Application was published in English on Nov. 30, 2006 as WO 2006/127298 A1 under PCT Article 21(2).

BACKGROUND OF THE INVENTION

1. Field of the Invention

This invention relates to a method of producing a suspended agricultural chemical composition which is stable even after being preserved it for a long time.

2. Description of Related Art

In recent years, agricultural chemical active ingredients of high permeability have been developed and brought to market, and methods of coating seeds with them are generally used for controlling pests and disease. In order to ensure the safety of workers when coating the seeds, and to improve efficiency when coating the seeds, aqueous suspended formulations containing high-concentrations of agricultural chemical active ingredients are required. However, it is necessary to suppress Ostwald ripening causing crystal growth during a long term preservation, in order to produce aqueous suspended formulations containing high-concentrations of agricultural chemical active ingredients having a high solubility in water at room temperature. In Patent Literature 1, suspended agricultural chemical compositions, in which water-insoluble agricultural chemical active ingredients are dispersed in organic solvents having a high affinity with water and exerting significant solubilization effects on the agricultural chemical active ingredients, are disclosed. In Patent Literature 2, suspended agricultural chemical compositions, in which water-soluble active ingredients are dispersed in organic solvents having a high affinity with water and containing a low content of water, are disclosed. In Patent Literature 3, oil-in-water emulsive agricultural chemical compositions containing 0.1 to 2.0% by weight of hydrated alumina (as $Al_2O_3$) and 0.1 to 20% by weight of mineral salts are disclosed. In Patent Literature 4, agricultural chemical compositions containing organic acids, inorganic acids, and/or salts thereof are disclosed.

Patent Literature 1 Japanease Unexamined Patent Application, First Publication No. Sho 57-109701 (corresponding to U.S. Pat. No. 4,348,385)

Patent Literature 2 U.S. Pat. No. 5,906,962

Patent Literature 3 Japanease Unexamined Patent Application, First Publication No. Hei 5-25011

Patent Literature 4 Japanease Unexamined Patent Application, First Publication No.

However, the invention disclosed in Patent Literature 1 is limited to water-insoluble agricultural chemical active ingredients. The method disclosed in Patent Literature 2 causes problems, such as increase of the viscosity of products, which decreases the efficiency of discharging them from bottles. The invention disclosed in Patent Literature 3 relates to emulsions in which the agricultural chemical active ingredients are limited to aqueous organophosphorus ingredients. Patent Literature 4 has as its object to suppress decomposition of the agricultural chemical active ingredients during storage, and does not disclose any effects of inhibiting particle growth of active ingredients in the suspended agricultural chemical compositions.

SUMMARY OF THE INVENTION

The present invention has for an object to provide methods of producing suspended agricultural chemical compositions which are stable even after they are preserved for a long time.

As a result of diligent studies to solve the above-mentioned problems, the inventors of the present invention have found methods of producing suspended agricultural chemical compositions which contain at least one agricultural chemical active ingredient, water, a polyalcohol, a mineral salt, a surfactant, and a suspension stabilizer.

The present invention provides a method of producing a suspended agricultural chemical composition, comprising the steps of: grinding an agricultural chemical active ingredient; mixing at least water, a polyalcohol, a mineral salt, and a surfactant to produce a solution; adding to the solution the ground agricultural chemical active ingredient and a suspension stabilizer to produce a mixture; heating the mixture to 40 to 70° C. while stirring; cooling the heated mixture to 10 to 25° C.; and wet-milling the cooled mixture at 30° C. or below.

Also, the present invention provides a method of producing a suspended agricultural chemical composition, comprising the steps of: grinding an agricultural chemical active ingredient; mixing at least water, a polyalcohol, a mineral salt, and a surfactant to produce a solution; adding to the solution the ground agricultural chemical active ingredient and a suspension stabilizer to produce a mixture; wet-milling the mixture; heating the wet-milled mixture to 40 to 70° C. while stirring; and cooling the heated mixture.

The polyalcohol may be glycerin.

The mineral salt may be any one of potassium chloride, sodium chloride, and sodium sulfate, or a mixture thereof.

The surfactant may be sodium lignin sulfonate.

The suspension stabilizer may be any one of white carbon, bentonite, and aluminium oxide, or a mixture thereof.

The agricultural chemical active ingredient may be an ingredient having solubility in water at 25° C. of 100 ppm or more.

The agricultural chemical active ingredient may be a neo nicotinoide base compound.

The neo nicotinoide base compound may be at least one selected from the group consisting of nitenpyram, imidacloprid, acetamiprid, thiamethoxiam, clotianidin, thiacloprid, and dinotefuran.

DETAILED DESCRIPTION OF THE INVENTION

The present invention provides the following methods for producing suspended agricultural chemical compositions (1) and (2).

According to method (1), water, a polyalcohol, a mineral salt, and a surfactant are mixed together and are dissolved. A mixture of an agricultural chemical active ingredient ground in advance and a dispersion stabilizer is added, and the combined mixture is then heated to 40 to 70° C. while stirring, followed by cooling it to 10 to 25° C., and then by wet-milling it at 30° C. or below.

The heating temperature is set within a range from 40 to 70° C., preferably 40 to 50° C. When the heating temperature is within a range from 40 to 70° C., Ostwald ripening causing crystal growth during a long term preservation of the agricultural chemical active ingredient having high solubility in water can be more effectively suppressed. The cooling temperature is set within a range from 10 to 25° C., preferably 18 to 23° C. When the cooling temperature is set within a range from 10 to 25° C., Ostwald ripening causing crystal growth during a long term preservation of the agricultural chemical active ingredient having high solubility in water can be more effectively suppressed. The wet-milling temperature is set at 30° C. or below, preferably below 25° C. When the wet-milling is set at 30° C. or below, Ostwald ripening causing crystal growth during a long term preservation of the agricultural chemical active ingredient having high solubility in water can be more effectively suppressed. The heating time, the cooling time, and the retaining time are not particularly limited. For example, after the temperature of the heated mixture attains the predetermined heating temperature, the heated mixture may be held at that temperature for any number of hours, or may be immediately cooled. The step of cooling the heated mixture may be carried out by leaving the mixture at room temperature to gradually cool it, or by using ice or the like to rapidly cool it. In this method (1), any mills may be used, provided that they have a cooling jacket for preventing increase of the temperature during wet-milling of the mixutre. Preferably, mills which can finely granulate the mixture are used. Examples of the mill include bead mills such as a Dyno-mill, an Eiger-mill, and the like. By using any one of these mills, the mixture is wet-milled while cooling at 30° C. or below, until its average particle diameter attains the predetermined particle diameter.

According to method (2), water, a polyalcohol, a mineral salt, and a surfactant are mixed together, and are dissolved. A mixture of an agricultural chemical active ingredient ground in advance and a dispersion stabilizer is added, and the combined mixture is then wet-milled, followed by heating it to 40 to 70° C. while stirring, and then by cooling it.

The heating temperature is set within a range from 40 to 70° C., preferably 45 to 50° C. When the heating temperature is within a range from 40 to 70° C., Ostwald ripening causing crystal growth during a long term preservation of the agricultural chemical active ingredient having high solubility in water can be more effectively suppressed. Although the cooling temperature is not particularly limited, the cooling temperature is preferably set within a range from 18 to 23° C. The heating time, the cooling time, and the retaining time are not particularly limited. For example, after the temperature of the heated mixture attains the predetermined heating temperature, the heated mixture may be held at that temperature for any number of hours, or may be immediately cooled. The step of cooling the heated mixture may be carried out by leaving the mixture at room temperature to gradually cool it, or by using ice or the like to rapidly cool it. Although the mills described for method (1) are preferable in method (2), any mills may be used, because method (2) does not impose limitations on the wet-milling temperature, provided that the mills are not non-functional at the wet-milling temperature.

In these methods, although the order of mixing the water, the polyalcohol, the mineral salt, and the surfactant is not particularly limited, the water, the polyalcohol, the mineral salt, and the surfactant are preferably mixed and dissolved in this order. More preferably, the mineral salt is mixed with the mixture of the water and the polyalcohol, to which the surfactant is mixed after the mineral salt is completely dissolved into the mixture.

The mixture of the agricultural chemical active ingredient and the suspension stabilizer should be ground by using a jet mill, a pin mill, or the like, until its average particle diameter becomes 50 μm or less, preferably 25 μm or less, and more preferably 10 μm or less. When the average particle diameter is 50 μm or less, the agricultural chemical active ingredients are more effectively prevented from enlarging their crystal form, as a result of which their permeability increases.

As the polyalcohol, any polyalcohols may be used, provided that they can be freely mixed with water, and are in a liquid form at 25° C. Although examples of the polyalcohol include glycerin, ethylene glycol, propylene glycol, diethylene glycol, dipropylene glycol, polyethylene glycol, and the like, the polyalcohol is not limited to these. The polyalcohol may be used alone, or may be a mixture of two or more kinds. Among these polyalcohols, glycerin is preferably used for producing the suspended agricultural chemical compositions of the present invention.

Although the amount of the polyalcohol contained in the suspended agricultural chemical composition may be determined according to kinds of the polyalcohol used, the content of other ingredients contained in the composition, and the like, the amount of the polyalcohol is preferably within a range from 18 to 23% by weight, relative to the total weight of the composition.

As the mineral salt, any materials may be used, provided that their solubility in water at 25° C. is 20% or more. When the solubility of the mineral salt is 20% or more, it may be sufficiently dissolved in the mixture. Examples of the mineral salt include chlorides, carbonates, sulfates, nitrates, and the like. Although sodium chloride, potassium chloride, magnesium chloride, calcium chloride, sodium carbonate, potassium carbonate, sodium sulfate, magnesium sulfate, ammonium sulfate, ammonium nitrate, and the like, may be specifically included, the mineral salt is not limited to these. The mineral salt may be used alone, or may be a mixture of two or more kinds. In particular, potassium chloride or sodium sulfate may be preferably used for producing the suspended agricultural chemical compositions of the present invention.

Although the amount of the mineral salt contained in the suspended agricultural chemical composition may be determined according to kinds of the mineral salt used, the content of other ingredients contained in the composition, and the like, the amount of the mineral salt is preferably within a range from 5 to 10% by weight, relative to the total weight of the composition.

As the surfactant, any materials may be used, provided that they are generally used for producing conventional agricultural chemical formulations. Specific examples of the surfactant include nonionic surfactants such as sugar ester type surfactants such as sorbitan fatty acid esters ($C_{12-18}$), POE sorbitan fatty acid esters ($C_{12-18}$), sucrose fatty acid esters, and the like, fatty acid ester type surfactants such as POE fatty acid esters ($C_{12-18}$), POE resinates, POE fatty acid diesters ($C_{12-18}$), and the like, alcohol type surfactants such as POE alkyl ethers ($C_{12-18}$), and the like, alkyl phenol type surfactants such as POE alkyl ($C_{8-12}$) phenyl ethers, POE dialkyl ($C_{8-12}$) phenyl ethers, POE alkyl ($C_{8-12}$) phenyl ether formalin condensation products, and the like, polyoxyethylene-polyoxypropylene block polymer type surfactants such as polyoxyethylene-polyoxypropylene block polymers, alkyl ($C_{12-18}$) polyoxyethylene-polyoxypropylene block polymer ethers, and the like, alkylamine type surfactants such as POE alkylamines ($C_{12-18}$), POE fatty amides ($C_{12-18}$), and the like, bisphenol type surfactants such as POE fatty acid bisphenyl ethers, and the like, polyaromatic ring type surfactants such as POA benzylphenyl (alternatively, phenylphenyl)ethers, POA styrylphenyl (alternatively, phenylphenyl)ethers, and the like, silicon or fluorine base surfactants such as POE ether or ester type silicon or fluorine base surfactants, and the like, vegetable oil type surfactants such as POE castor oils, POE hardened castor oils, and the like, anionic surfactants such as sulphate type surfactants such as alkyl sulphates ($C_{12-18}$, Na, $NH_4$, alkanolamine), POE alkylether sulphates ($C_{12-18}$, Na, $NH_4$, alkanolamine), POE alkylphenyl ether sulphates ($C_{12-18}$, $NH_4$, alkanolamine, Ca), POE benzyl (alternatively, styryl) phenyl (alternatively, phenylphenyl)ether sulphates (Na, $NH_4$, alkanolamine), polyoxyethylene, polyoxypropylene block polymer sulphates (Na, $NH_4$, alkanolamine), and the like, sulfonate type surfactants such as paraffin (alkane) sulfonates ($C_{12-22}$, Na, Ca, alkanolamine), AOS ($C_{14-16}$, Na, alkanolamine), dialkyl sulfosuccinates ($C_{8-12}$, Na, Ca, Mg), alkylbenzene sulfonates ($C_{12}$, Na, Ca, Mg, $NH_4$, alkylamine, alkanol, amine, cyclohexyl amine), mono- or di-alkyl ($C_{3-6}$) naphthalene sulfonates (Na, $NH_4$, alkanolamine, Ca, Mg), naphthalene sulfonate-formalin condensation products (Na, $NH_4$), alkyl ($C_{8-12}$) diphenyl ether disulfonates (Na, $NH_4$), lignin sulfonates (Na, Ca), POE alkyl ($C_{8-12}$) phenyl ether sulfonates (Na), POE alkyl ($C_{12-18}$) ether sulfosuccinic acid half esters (Na), and the like, carboxylic acid type fatty acid salts ($C_{12-18}$, Na, K, $NH_4$, alkanolamine), N-methyl-fatty acid sarcosinate ($C_{12-18}$, Na), phosphate type surfactants such as POE alkyl ($C_{12-18}$) ether phosphates (Na, alkanolamine) such as resinates (Na, K), POE mono- or di-alkyl ($C_{8-12}$) phenyl ether phosphates (Na, alkanolamine), POE benzylated (alternatively, styrylated) phenyl (alternatively, phenylphenyl) ether phosphates (Na, alkanolamine), polyoxyethylene-polyoxypropylene block polymers (Na, alkanolamine), phosphatidyl choline phosphatidyl ethanolimines (lecithin), alkyl ($C_{8-12}$) phosphates, and the like, cationic surfactants such as ammonium type surfactants such as alkyl trimethyl ammonium chlorides ($C_{12-18}$), methyl polyoxyethylene alkylammonium chlorides ($C_{12-18}$), alkyl N-methylpyridium bromides ($C_{12-18}$), mono- or di-alkyl ($C_{12-18}$) methylated ammonium chlorides, alkyl ($C_{12-18}$) pentamethyl propylene diamine dichlorides, and the like, benzalkonium type surfactants such as alkyldimethyl benzalkonium chlorides ($C_{12-18}$), benzethonium chlorides (octylphenoxy ethoxyethyl dimethylbenzyl ammonium chlorides), and the like, amphoteric surfactants such as betaine type surfactants such as dialkyl ($C_{8-12}$) diaminoethyl betaine, alkyl ($C_{12-18}$) dimethylbenzyl betaine, and the like, glycine type surfactants such as dialkyl ($C_{8-12}$) diaminoethyl glycine, alkyl ($C_{12-18}$) dimethylbenzyl glycine, and the like. These may be respectively used alone, or may be mixed together with two or more kind. Among these surfactants, anionic surfactans, specifically lignin sulfonate (Na, Ca) is preferably used for producing the suspended agricultural chemical compositions of the present invention.

Although the amount of the surfactant contained in the suspended agricultural chemical composition may be determined according to kinds of the surfactant used, the content of other ingredients contained in the composition, and the like, the amount of the surfactant is preferably within a range from 3 to 6% by weight, relative to the total weight of the composition.

As the suspension stabilizer used in the present invention, any materials may be used, provided that they are conventionally added to suspended agricultural chemical compositions for the purpose of stabilizing suspensibility of particles in water. Although carriers such as bentonites, white carbons, aluminium oxides, or the like, water-soluble high polymers such as xanthan gums, guar gums, carboxymethyl celluloses, or the like, or polymers which are freely soluble in solvents such as polyvinyl pyrolidone, methoxypolyethylene oxide methacrylate, or the like, which easily absorb particles, may be specifically used, the suspension stabilizer is not limited to these. These may be used alone, or may be a mixture of two or more kinds. Among these, white carbons, bentonites, or aluminium oxides are preferably used.

Although the amount of the suspension stabilizer contained in the suspended agricultural chemical composition may be determined according to kinds of the suspension stabilizer used, the content of other ingredients contained in the composition, and the like, the amount of the suspension stabilizer contained in the suspended agricultural chemical composition is preferably within a range from 0.5 to 1.5% by weight, relative to the total weight of the composition.

The agricultural chemical active ingredient used in the present invention may be liquid or solid, an organic compound or an inorganic compound, a single compound or a mixture, and so forth. Specifically, examples of the agricultural chemical active ingredient include the following fungicides, insecticides, acaricides, plant growth regulators, herbicides, and the like. These agricultural chemical active ingredients may be used alone, or may be mixed.

Fungicides:

Copper agents: basic copper chlorides, basic copper sulfates, and the like.

Sulfur agents: thiuram, zineb, maneb, mancozeb, ziram, propineb, polycarbamate, and the like.

Polyhaloalkylthio agents: captan, folpet, dichlorfluanido, and the like.

Organic chlorine agents: chlorothalonil, phthalide, and the like.

Organophosphorous agents: IBP, EDDP, trichlofos methyl, pyrazophos, fosetyl, and the like.

Benzimidazol agents: thiophanate-methyl, benomyl, carbendazim, tiabendazole, and the like.

Dicarboxyimide agents: iprodione, procymidone, vinclozolin, fluoroimide, and the like.

Carboxyamide agents: oxycarboxin, mepronil, flutolanil, tecloftalam, trichlamide, pencycuron, and the like.

Acyl alanine agents: metalaxyl, oxadixyl, furalaxyl, and the like.

Methoxyacrylate agents: kresoxim-methyl, azoxystrobin, metominostrobin, and the like.

Anilinopyrimidine agents: mepanipyrim, pyrimethanil, cyprodinil, and the like.

SBI agents: triadimefon, triadimenol, bitertanol, myclobutanil, hexaconazole, propiconazole, triflumizole, prochloraz, pefurazoate, fenarimole, pirifenox, triforine, flusilazole, etaconazole, diclobutrazol, fluotrimazole, flutriafen, penconazole, diniconazole, imazalil, tridemorph, fenpropimorph, buthiobate, epoxyconazole, methoconazole, and the like.

Antibiotic agents: polyoxine, blasticiden S, kasugamycine, validamycine, streptomycin dihydrosulphate, and the like.

Others: puropamocarb hydrochlorid, quintozene, hydroxy isoxazole, methasulfocarb, anilazine, isoprothiolane, probenazole, quinomethionate, dithianone, dinocab, diclomezine, ferimzone, fluazinam, pyroquilon, tricyclazole, oxolinic acid, dithianone, iminoctadine triacetate, cymoxanil, pyrrolnitrin, methasulfocarb, diethofencarb, binapacryl, lecithin, sodium bicarbonate, fenaminosulf, dozine, dimetomorph, phenadine oxide, carpropamide, flusulphamide, fludioxonile, famoxadone, and the like.

Insecticides and Acaricides:

Organophosphate and carbamate base insecticides: fenthion, fenitrothion, diazinon, chlorpyrifos, ESP, vamidothion, phenthoate, dimetoate, formothion, marathon, trichlorfon, thiometon, phosmet, dichlorvos, acephate, EPBP, methyl parathion, oxydimethone methyl, ethion, salithion, cyanophos, isoxathion, pyridafenthion, phosalone, methidathion, sulprofos, chlorfenvinphos, tetra chlorvinphos, dimethylvinphos, propaphos, isofenphos, ethyl thiometon, profenofos, pyraclofos, monochlotophos, azinphos methyl, ardicarb, methomyl, thiodicarb, carbofuran, carbosulphan, benfuracarb, furathiocarb, propoxur, BPMC, MTMC, MIPC, carbaryl, pirimicarb, ethiophencarb, phenoxycarb, and the like.

Pyrethroid base insecticides: permethrin, cypermethrin, deltamethrin, fenvalerate, fenpropathrin, pyrethrins, allethrin, tetra methrin, resmethrin, dimethrin, propathrin, phenotrin, prothrin, fluvalinate, cyfluthrin, cyhalothrin, flucythrinate, ethofenprox, cycloprothrin, tralomethrin, silafluofen, brofenprox, acrinathrin, and the like.

Benzoylurea base and other insecticides: diflubenzuron, chlorfluazuron, hexaflumuron, triflumuron, tetra benzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, microbial agrichemicals such as BT and insect pathogenic viruses, and the like.

Nematocides: phenamiphos, fosthiazate, and the like.

Acaricides: chlorobenzilate, phenisobromolate, dicofol, amitraz, BPPS, benzomate, hexathiazox, fenbutatin oxide, polynactins, quinomethionate, CPCBS, tetradifone, avermectin, milbemectin, clofentezine, cyhexatin, pyridaben, fenpyroximate, tebufenpyrad, pyrimidifen, phenothiocarb, dienochlor, and the like.

Plant growth regulators: gibberellins (for example, gibberellin A3, gibberellin A4, giebbrellin A7), IAA, NAA, and the like.

Herbicides:

Anilide base herbicides: diflufenican, propanyl, and the like.

Chloroacetoanilide base herbicides: alachlor, pretilachlor, and the like.

Aryloxyalkane acid base herbicides: 2,4-D,2,4-DB, and the like.

Aryloxyphenoxy alkane acid base herbicides: dichlofop-methyl, phenoxaprop-ethyl, and the like.

Arylcarboxylic acid base herbicides: dicamba, pyrithiobac, and the like.

Imidazoline base herbicides: imazaquin, imazethapyr, and the like.

Urea base herbicides: diuron, isoproturon, and the like.

Carbamate base herbicides: chlorpropham, phenmedipham, and the like.

Thiocarbamate base herbicides: thiobencarb, EPTC, and the like.

Dinitroaniline base herbicides: trifluralin, pendimethalin, and the like.

Diphenyl ether base herbicides: acifluorfen, fomesafen, and the like.

Sulphonylure base herbicides: bensulfuron-methyl, nicosulfuron, and the like.

Triadinone base herbicides: metribuzin, metamitron, and the like.

Triadine base herbicides: atrazine, cyanazine, and the like.

Triazo pyrimidine base herbicides: flumetsulam, and the like.

Nitrile base herbicides: bromoxynil, dichlobenzyl, and the like.

Phosphate base herbicides: glyphosate, glyphosinate, and the like.

Quaternary ammonium salt base herbicides: paraquat, difenzoquat, and the like.

Cyclic imide base herbicides: flumiclorac-pentyl, fluthiacet-methyl, and the like.

Benzoylamino propionic acid base herbicides: benzoylprop-ethyl, flamprop-methyl, and the like.

Other herbicides: isoxaben, ethofumesate, oxadiazone, piperophos, daimuron, bentazone, benfuresate, difenzoquat, naproanilide, triazo phenamide, quinclorac, clomazone, sulcotrione, cinmethylin, dithiopyr, pyrazolate, pyridate, flupoxam, and cyclohexadione base herbicides such as sethoxydim, tralkoxydim, and the like.

Although the amount of the agricultural chemical active ingredient contained in the suspended agricultural chemical composition may be determined according to kinds of the agricultural chemical active ingredient used, the content of other ingredients contained in the composition, and the like, the amount of the agricultural chemical active ingredient is preferably within a range from 10 to 50% by weight, relative to the total weight of the composition. It is preferable to increase the concentration of the agricultural chemical active ingredient from the view point of physical properties of the composition. In contrast, it is preferable to decrease the concentration of the agricultural chemical active ingredient from the view point of distribution cost.

According to the method of producing the suspended agricultural chemical compositions of the present invention, it is possible to produce a suspended agricultural chemical composition which is stable for a long time, even if it contains agricultural chemical active ingredients having high solubility in water at 25° C., particularly solubility of 100 ppm or more, and more particularly 500 ppm or more.

Examples of agricultural chemical active ingredients having a high solubility in water at 25° C. include neo nicotinoide base compounds such as nitenpyram, imidacloprid, acetamiprid, thiamethoxiam, clotianidin, thiacloprid, dinotefuran, and the like.

The suspended agricultural chemical compositions may include an agricultural chemical active ingredient having low solubility in water at 25° C., in addition to the agricultural chemical active ingredient having high solubility in water at 25° C.

According to the method of producing the suspended agricultural chemical compositions of the present invention, the compositions may be produced by adding coloring ingredients such as dyes, pigments, or the like, if needed.

EXAMPLES

In the following, the present invention will be explained in more detail by way of Preparation Examples and Formulation Examples, but the scope of the present invention should not be interpreted to be limited to these examples.

Preparation Example 1

Preparation of a Ground Mixture of an Active Ingredient and a Suspension Stabilizer After 1.203 g of an acetamiprid active ingredient, 3 g of HiSil SC72 (white carbon manufactured by LIANJI CHEMICAL INDASTRY Co., Ltd.), 15 g of AEROXIDE Alu C (aluminium oxide manufactured by Nippon Aerosil Co., Ltd.), and 6 g of Attagel 50 (bentonite manufactured by Hayashi Kasei Co, Ltd.) were mixed thoroughly in a plastic bag, they were ground by means of a jet mill (4B WellMax manufactured by NISSO ENGINIEERING CO., LTD.) to produce fine particles of which average particle diameter was 21 μm. All of the average particle diameters in this specification were determined by measuring their volume average particle diameter by means of a MicroTrack 9320-X-100 manufactured by NIKKISO Co., Ltd.

Preparation Example 2

Preparation of Dissolved Mixture of Water, a Polyalcohol, a Mineral Salt, and a Surfactant After 627 g of distilled water and 350 g of glycerin were put into a 5 L stainless cylindrical container, a stirrer was fixed in the container, and was then rotated at 1,000 rpm, to mix and dissolve them. Into this container, 126 g of potassium chloride was put, and was then stirred until it was completely dissolved. Next, 75 g of Lignosol SFX-65 (sodium lignin sulfonate manufactured by LIGNOTECH USA CO., LTD.) was added, and was then stirred until it was completely dissolved.

Preparation Example 3

Preparation of a Suspended Agricultural Chemical Composition 1

818 g of the ground mixture produced in Preparation Example 1 was gradually added to the dissolved mixture produced in Preparation Example 2, and was then heated to 45° C. while stirring at 6,000 rpm to 7,000 rpm until it was uniformly dispersed in the dissolved mixture. When its liquid temperature reached 45° C., the container was immediately immersed in ice water to cool it to 21° C. The cooled mixture was then milled while cooling to prevent its temperature from exceeding 25° C. by circulating cooling water at 5° C. through a cooling jacket of a milling portion of a wet-milling machine (Dyno mill KLD type manufactured by Willy A. Bachofen Co., Ltd.) to produce a suspended agricultural chemical composition.

Formulation Example 1

According to Preparation Examples 1 to 3, a suspended agricultural chemical composition was produced.

Formulation Examples 2 to 5

According to Preparation Examples 1 to 3, suspended agricultural chemical compositions of Formulation Examples 2 to 5 were produced by using various kinds of polyalcohols, mineral salts, and surfactants at various concentrations, which are different from those of the composition of Formulation Example 1, as shown in Table 1.

Preparation Example 4

Preparation of a Suspended Agricultural Chemical Composition 2

818 g of the ground mixture produced in Preparation Example 1 was gradually added to the dissolved mixture produced in Preparation Example 2, and was then stirred at 6,000 rpm to 7,000 rpm until it was uniformly dispersed in the dissolved mixture. This suspension was milled by means of a wet-milling machine (Dyno mill KLD type manufactured by Willy A. Bachofen Co., Ltd.), and was then put into a stainless steel container, and was then heated to 45° C. by using a band heater, while stirring by using a stirrier provided with the container. When its liquid temperature reached 45° C., the band heater was removed, and the heated suspension was further stirred until its liquid temperature cooled to room temperature to produce a suspended agricultural chemical composition.

Formulation Examples 6 to 10

According to Preparation Examples 1, 2 and 4, suspended agricultural chemical compositions of Formulation Examples 6 to 10 were produced by using various kinds of polyalcohols, mineral salts, and surfactants at various concentrations, which were similar to those of the compositions of Formulation Examples 1 to 5, as shown in Table 2.

Comparative Formulation Examples 1 to 5

According to Preparation Examples 1 to 3, suspended agricultural chemical compositions of Comparative Formulation Examples 1 to 5 were produced by using various kinds of polyalcohols, mineral salts, and surfactants at various concentrations, which were different from those of the composition of Formulation Example 1, as shown in Table 3.

Comparative Formulation Examples 6 and 7

According to Preparation Examples 1, 2 and 4, suspended agricultural chemical compositions of Comparative Formulation Examples 6 and 7 were produced by using various kinds of polyalcohols, mineral salts, and surfactants at various concentrations, which were similar to those of the compositions of Comparative Formulation Examples 1 and 2, as shown in Table 4.

Comparative Preparation Example 1

Preparation of a Mixture of an Active Ingredient and a Suspension Stabilizer 1.203 g of an acetamiprid active ingredient, 3 g of HiSil SC72 (white carbon manufactured by LIANJI CHEMICAL INDASTRY Co., Ltd.), 15 g of AEROXIDE Alu C (aluminium oxide manufactured by Nippon Aerosil Co., Ltd.), and 6 g of Attagel 50 (bentonite manufactured by Hayashi Kasei Co, Ltd.) were mixed thoroughly in a plastic bag. They were not ground.

Comparative Preparation Example 2

Preparation of a Suspended Agricultural Chemical Composition 3

818 g of the mixture produced in Comparative Preparation Example 1 was gradually added to the dissolved mixture produced in Preparation Example 2, and was then heated to 45° C. by means of a band heater, while stirring at 6,000 rpm to 7,000 rpm, until it was uniformly dispersed in the dissolved mixture. When its liquid temperature reached 45° C., its container was immediately immersed in ice water to cool it to 21° C. The cooled mixture was then milled while cooling to prevent its temperature from exceeding 25° C. by circulating cooling water at 5° C. through a cooling jacket of a milling portion of a wet-milling machine (Dyno mill KLD type manufactured by Willy A. Bachofen Co., Ltd.) to produce a suspended agricultural chemical composition.

Comparative Preparation Example 3

Preparation of a Suspended Agricultural Chemical Compositions 4

818 g of the ground mixture produced in Preparation Example 1 was gradually added to the dissolved mixture produced in Preparation Example 2, and was then stirred at 6,000 rpm to 7,000 rpm, until it was uniformly dispersed in the dissolved mixture. This suspension was then milled by using a wet-milling machine (Dyno mill KLD type manufactured by Willy A. Bachofen Co., Ltd.) to produce a suspended agricultural chemical composition.

Comparative Preparation Example 4

Preparation of a Suspended Agricultural Chemical Compositions 5

818 g of the mixture produced in Comparative Preparation Example 1 was gradually added to the dissolved mixture produced in Preparation Example 2, and was then stirred at 6,000 rpm to 7,000 rpm, until it was uniformly dispersed in the dissolved mixture. This suspension was milled by means of a wet-milling machine (Dyno mill KLD type manufactured by Willy A. Bachofen Co., Ltd.), and was then put into a stainless steel container, and was then heated to 45° C. by using a band heater, while stirring by a stirrier provided with the container. When its liquid temperature reached 45° C., the band heater was removed, and the heated mixture was further stirred until its liquid temperature was cooled to room temperature to produce a suspended agricultural chemical composition.

Comparative Formulation Examples 8 to 10

According to Preparation Examples 1 and 2 and Comparative Preparation Examples 2 to 4, suspended agricultural chemical compositions of Comparative Formulation Examples 11 and 13 were produced by using various kinds of polyalcohols, mineral salts, and surfactants at various concentrations, which were similar to those of the compositions of Formulation Examples 1 to 3, as shown in Table 4.

Test Example 1

External forms of the suspended agricultural chemical compositions measured immediately after preparation thereof were evaluated according to the following criteria, and their volume average particle diameters were measured by using a MicroTrack 9320-X-100 manufactured by NIKKISO Co., Ltd.

O: excellent flowability as a suspended agricultural chemical composition

X: Unexcellent flowability as a suspended agricultural chemical composition

Test Example 2

After each of the produced suspended agricultural chemical compositions was put into a glass bottle having a diameter of 2.5 cm and a high of 11 cm, which was then sealed, followed by storing it in an incubator at 54° C. for 14 days, an external form of each of the suspended agricultural chemical compositions was evaluated according to the same criteria as in Test Example 1, and their volume average particle diameter was measured by using a MicroTrack 9320-X-100 manufactured by NIKKISO Co., Ltd.

TABLE 1

| Ingredient | Type | Formulation Example 1 | Formulation Example 2 | Formulation Example 3 | Formulation Example 4 | Formulation Example 5 |
|---|---|---|---|---|---|---|
| Acetamiprid | Active ingredient | 40.1% | 40.1% | 32% | 40.1% | 40.1% |
| Glycerin | Polyalcohol | 17.5% | 17.5% | 19% | — | — |
| Ethylene Glycol | Polyalcohol | — | — | — | 22.5% | — |
| Propylene Glycol | Polyalcohol | — | — | — | — | 16.5% |
| Potassium Chloride | Mineral salt | 6.3% | — | — | 6.3% | 6.3% |
| Sodium Chloride | Mineral salt | — | 8.0% | — | — | — |
| Sodium Sulfate | Mineral salt | — | — | 9.5% | — | — |
| Lignolsol SFX-65 | Surfactant | 3.75% | 3.5% | 3.0% | — | — |
| NEWKALGEN PS-P | Surfactant | — | — | — | 4.75% | — |
| SOPROPHOR FLK | Surfactant | — | — | — | — | 5.5% |
| Hi-Sil SC 72 | Suspension stabilizer | 0.1% | 0.1% | — | 0.1% | — |
| Hi-Sil SC 60L | Suspension stabilizer | — | — | 0.1% | — | 0.1% |
| Aluminum Oxide | Suspension stabilizer | 0.5% | 0.5% | 0.3% | 0.5% | 0.3% |
| Attagel 50 | Suspension stabilizer | 0.2% | 0.2% | 0.5% | 0.2% | 0.2% |
| Water | Medium | 31.55% | 30.10% | 35.60% | 25.55% | 31.00% |
| | Total | 100.0% | 100.0% | 100.0% | 100.0% | 100.0% |
| Preparation Method | Preparation of ground mixture of active ingredient and suspension stabilizer | Preparation Example 1 | Preparation Example 1 | Preparation Example 1 | Preparation Example 1 | Preparation Example 1 |
| | Preparation of dissolved mixture | Preparation Example 2 | Preparation Example 2 | Preparation Example 2 | Preparation Example 2 | Preparation Example 2 |

TABLE 1-continued

| Ingredient | Type | Formulation Example 1 | Formulation Example 2 | Formulation Example 3 | Formulation Example 4 | Formulation Example 5 |
|---|---|---|---|---|---|---|
| | Preparation of suspended agricultural chemical composition | Preparation Example 3 | Preparation Example 3 | Preparation Example 3 | Preparation Example 3 | Preparation Example 3 |
| (Evaluation) Immediately | Condition of suspension | ○ | ○ | ○ | ○ | ○ |
| after preparation | Average particle diameter | 5.5 µm | 4.8 µm | 5.3 µm | 5.6 µm | 6.0 µm |
| After preservation at | Condition of suspension | ○ | ○ | ○ | ○ | ○ |
| 54° C. for 14 days | Average particle diameter | 6.2 µm | 6.4 µm | 6.2 µm | 6.8 µm | 7.2 µm |

TABLE 2

| Ingredient | Type | Formulation Example 6 | Formulation Example 7 | Formulation Example 8 | Formulation Example 9 | Formulation Example 10 |
|---|---|---|---|---|---|---|
| Acetamiprid | Active ingredient | 40.1% | 40.1% | 32% | 40.1% | 40.1% |
| Glycerin | Polyalcohol | 17.5% | 17.5% | 19% | — | — |
| Ethylene Glycol | Polyalcohol | — | — | — | 22.5% | — |
| Propylene Glycol | Polyalcohol | — | — | — | — | 16.5% |
| Potassium Chloride | Mineral salt | 6.3% | — | — | 6.3% | 6.3% |
| Sodium Chloride | Mineral salt | — | 8.0% | — | — | — |
| Sodium Sulfate | Mineral salt | — | — | 9.5% | — | — |
| Lignolsol SFX-65 | Surfactant | 3.75% | 3.5% | 3.0% | — | — |
| NEWKALGEN PS-P | Surfactant | — | — | — | 4.75% | — |
| SOPROPHOR FLK | Surfactant | — | — | — | — | 5.5% |
| Hi-Sil SC 72 | Suspension stabilizer | 0.1% | 0.1% | — | 0.1% | — |
| Hi-Sil SC 60L | Suspension stabilizer | — | — | 0.1% | — | 0.1% |
| Aluminum Oxide | Suspension stabilizer | 0.5% | 0.5% | 0.3% | 0.5% | 0.3% |
| Attagel 50 | Suspension stabilizer | 0.2% | 0.2% | 0.5% | 0.2% | 0.2% |
| Water | Medium | 31.55% | 30.10% | 35.60% | 25.55% | 31.00% |
| | Total | 100.0% | 100.0% | 100.0% | 100.0% | 100.0% |
| Preparation Method | Preparation of ground mixture of active ingredient and suspension stabilizer | Preparation Example 1 | Preparation Example 1 | Preparation Example 1 | Preparation Example 1 | Preparation Example 1 |
| | Preparation of dissolved mixture | Preparation Example 2 | Preparation Example 2 | Preparation Example 2 | Preparation Example 2 | Preparation Example 2 |
| | Preparation of suspended agricultural chemical composition | Preparation Example 4 | Preparation Example 4 | Preparation Example 4 | Preparation Example 4 | Preparation Example 4 |
| (Evaluation) Immediately | Condition of suspension | ○ | ○ | ○ | ○ | ○ |
| after preparation | Average particle diameter | 6.2 µm | 6.8 µm | 6.5 µm | 5.8 µm | 7.3 µm |
| After preservation at | Condition of suspension | ○ | ○ | ○ | ○ | ○ |
| 54° C. for 14 days | Average particle diameter | 7.5 µm | 8.0 µm | 7.7 µm | 6.8 µm | 8.3 µm |

TABLE 3

| Ingredient | Type | Comparative Formulation Example 1 | Comparative Formulation Example 2 | Comparative Formulation Example 3 | Comparative Formulation Example 4 | Comparative Formulation Example 5 |
|---|---|---|---|---|---|---|
| Acetamiprid | Active ingredient | 40.1% | 40.1% | 40% | 32.0% | 40.1% |
| Glycerin | Polyalcohol | 17.5% | — | — | — | — |
| Ethylene Glycol | Polyalcohol | — | — | 22.5% | — | — |
| Propylene Glycol | Polyalcohol | — | — | — | 17.0% | — |
| Potassium Chloride | Mineral salt | — | 6.3% | — | — | — |
| Sodium Sulfate | Mineral salt | — | — | — | — | 9.5% |
| Lignolsol SFX-65 | Surfactant | 3.75% | — | 3.5% | 3.0% | — |
| NEWKALGEN PS-P | Surfactant | — | 4.75% | — | — | — |
| SOPROPHOR FLK | Surfactant | — | — | — | — | 5.5% |
| Hi-Sil SC 72 | Suspension stabilizer | 0.1% | 0.1% | 0.1% | — | — |
| Hi-Sil SC 60L | Suspension stabilizer | — | — | — | 0.1% | 0.1% |
| Aluminum Oxide | Suspension stabilizer | 0.5% | 0.5% | 0.5% | 0.3% | 0.3% |
| Attagel 50 | Suspension stabilizer | 0.2% | 0.2% | 0.2% | 0.5% | 0.2% |
| Water | Medium | 37.85% | 48.05% | 33.10% | 47.10% | 44.30% |
| Total | | 100.0% | 100.0% | 100.0% | 100.0% | 100.0% |
| Preparation Method | Preparation of ground mixture of active ingredient and suspension stabilizer | Preparation Example 1 | Preparation Example 1 | Preparation Example 1 | Preparation Example 1 | Preparation Example 1 |
| | Preparation of dissolved mixture | Preparation Example 2 | Preparation Example 2 | Preparation Example 2 | Preparation Example 2 | Preparation Example 2 |
| | Preparation of suspended agricultural chemical composition | Preparation Example 3 | Preparation Example 3 | Preparation Example 3 | Preparation Example 3 | Preparation Example 3 |
| (Evaluation) Immediately | Condition of suspension | ○ | ○ | ○ | ○ | ○ |
| after preparation | Average particle diameter | 3.3 μm | 6.3 μm | 4.2 μm | 3.5 μm | 6.6 μm |
| After preservation at | Condition of suspension | X | X | X | X | X |
| 54° C. for 14 days | Average particle diameter | Unmeasurable | Unmeasurable | Unmeasurable | Unmeasurable | Unmeasurable |

TABLE 4

| Ingredient | Type | Comparative Formulation Example 6 | Comparative Formulation Example 7 | Comparative Formulation Example 8 | Comparative Formulation Example 9 | Comparative Formulation Example 10 |
|---|---|---|---|---|---|---|
| Acetamiprid | Active ingredient | 40.1% | 40.1% | 40% | 40.1% | 40.1% |
| Glycerin | Polyalcohol | 17.5% | — | 18% | 18% | 17.5% |
| Ethylene Glycol | Polyalcohol | — | — | — | — | — |
| Propylene Glycol | Polyalcohol | — | — | — | — | — |
| Potassium Chloride | Mineral salt | — | 6.3% | 6.3% | 6.3% | 6.3% |
| Sodium Sulfate | Mineral salt | — | — | — | — | — |
| Lignolsol SFX-65 | Surfactant | 3.75% | — | 3.8% | 3.75% | 3.75% |
| NEWKALGEN PS-P | Surfactant | — | 4.75% | — | — | — |
| SOPROPHOR FLK | Surfactant | — | — | — | — | — |
| Hi-Sil SC 72 | Suspension stabilizer | 0.1% | 0.1% | 0.1% | 0.1% | 0.1% |
| Hi-Sil SC 60L | Suspension stabilizer | — | — | — | — | — |
| Aluminum Oxide | Suspension stabilizer | 0.5% | 0.5% | 0.5% | 0.5% | 0.5% |

TABLE 4-continued

| Ingredient | Type | Comparative Formulation Example 6 | Comparative Formulation Example 7 | Comparative Formulation Example 8 | Comparative Formulation Example 9 | Comparative Formulation Example 10 |
|---|---|---|---|---|---|---|
| Attagel 50 | Suspension stabilizer | 0.2% | 0.2% | 0.2% | 0.2% | 0.2% |
| Water | Medium | 37.85% | 48.05% | 31.55% | 31.55% | 31.55% |
| Total | | 100.0% | 100.0% | 100.0% | 100.0% | 100.0% |
| Preparation Method | Preparation of ground mixture of active ingredient and suspension stabilizer | Preparation Example 1 | Preparation Example 1 | Preparation Example 1 | Preparation Example 1 | Preparation Example 1 |
| | Preparation of dissolved mixture | Preparation Example 2 | Preparation Example 2 | Preparation Example 2 | Preparation Example 2 | Preparation Example 2 |
| | Preparation of suspended agricultural chemical composition | Preparation Example 4 | Preparation Example 4 | Preparation Example 2 | Preparation Example 3 | Preparation Example 4 |
| (Evaluation) Immediately after preparation | Condition of suspension | ○ | ○ | ○ | ○ | ○ |
| | Average particle diameter | 22 μm | 28 μm | 24 μm | 55 μm | 27 μm |
| After preservation at 54° C. for 14 days | Condition of suspension | X | X | X | X | X |
| | Average particle diameter | Unmeasurable | Unmeasurable | Unmeasurable | Unmeasurable | Unmeasurable |

As mentioned above, the methods of producing the suspended agricultural chemical compositions of the present invention are useful for producing aqueous suspended formulations containing high-concentrations of agricultural chemical active ingredients, which are safely and effectively used for coating seeds. In particular, according to the methods, it is possible to produce suspended agricultural chemical compositions in which Ostwald ripening causing crystal growth during a long term storage is suppressed, and in which the agricultural chemical active ingredient has a high solubility in water at room temperature, as a result of which permeability of the agricultural chemical active ingredients is raised, which further increases the efficiency of coating seeds.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of producing a suspended agricultural chemical composition, comprising the steps of:
- grinding an agricultural chemical active ingredient;
- mixing at least
  - water,
  - a polyalcohol,
  - a mineral salt, and
  - a surfactant to produce a solution;
- adding to the solution the ground agricultural chemical active ingredient and a suspension stabilizer, to produce a mixture;
- heating the mixture to 40 to 70° C. while stirring;
- cooling the heated mixture to 10 to 25° C.; and
- wet-milling the cooled mixture at 30° C. or below.

2. A method of producing a suspended agricultural chemical composition, comprising the steps of:
- grinding an agricultural chemical active ingredient;
- mixing at least
  - water,
  - a polyalcohol,
  - a mineral salt, and
  - a surfactant to produce a solution;
- adding to the solution the ground agricultural chemical active ingredient and a suspension stabilizer to produce a mixture;
- wet-milling the mixture;
- heating the wet-milled mixture to 40 to 70° C. while stirring; and
- cooling the heated mixture.

3. A method of producing a suspended agricultural chemical composition according to claim 1, wherein the polyalcohol is glycerin.

4. A method of producing a suspended agricultural chemical composition according to claim 2, wherein the polyalcohol is glycerin.

5. A method of producing a suspended agricultural chemical composition according to claim 1, wherein the mineral salt is any one of potassium chloride, sodium chloride, and sodium sulfate, or a mixture thereof.

6. A method of producing a suspended agricultural chemical composition according to claim 2, wherein the mineral salt is any one of potassium chloride, sodium chloride, and sodium sulfate, or a mixture thereof.

7. A method of producing a suspended agricultural chemical composition according to claim 1, wherein the surfactant is sodium lignin sulfonate.

8. A method of producing a suspended agricultural chemical composition according to claim 2, wherein the surfactant is sodium lignin sulfonate.

9. A method of producing a suspended agricultural chemical composition according to claim 1, wherein the suspension stabilizer is any one of white carbon, bentonite, and aluminium oxide, or a mixture thereof.

10. A method of producing a suspended agricultural chemical composition according to claim 2, wherein the suspension stabilizer is any one of white carbon, bentonite, and aluminium oxide, or a mixture thereof.

11. A method of producing a suspended agricultural chemical composition according to claim 1, wherein the agricultural chemical active ingredient has solubility in water at 25° C. of 100 ppm or more.

12. A method of producing a suspended agricultural chemical composition according to claim 2, wherein the agricultural chemical active ingredient has solubility in water at 25° C. of 100 ppm or more.

13. A method of producing a suspended agricultural chemical composition according to claim 1, wherein the agricultural chemical active ingredient is a neo nicotinoide base compound.

14. A method of producing a suspended agricultural chemical composition according to claim 2, wherein the agricultural chemical active ingredient is a neo nicotinoide base compound.

15. A method of producing a suspended agricultural chemical composition according to claim 13, wherein the neo nicotinoide base compound is at least one selected from the group consisting of nitenpyram, imidacloprid, acetamiprid, thiamethoxiam, clotianidin, thiacloprid, and dinotefuran.

16. A method of producing a suspended agricultural chemical composition according to claim 14, wherein the neo nicotinoide base compound is at least one selected from the group consisting of nitenpyram, imidacloprid, acetamiprid, thiamethoxiam, clotianidin, thiacloprid, and dinotefuran.

17. A method of producing a suspended agricultural chemical composition according to claim 1, wherein the mixture is heated to 45 to 50° C. in the step of heating the mixture while stirring.

18. A method of producing a suspended agricultural chemical composition according to claim 2, wherein the wet-milled mixture is heated to 45 to 50° C. in the step of heating the wet-milled mixture while stirring.

19. A method of producing a suspended agricultural chemical composition according to claim 1, wherein in the step of mixing at least the water, polyalcohol, mineral salt, and surfactant to produce a solution, the mixing and dissolving are done in an order of the water, then the polyalcohol, then the mineral salt, and then the surfactant.

20. A method of producing a suspended agricultural chemical composition according to claim 2, wherein in the step of mixing at least the water, polyalcohol, mineral salt, and surfactant to produce a solution, the mixing and dissolving are done in an order of the water, then the polyalcohol, then the mineral salt, and then the surfactant.

* * * * *